(12) United States Patent
Nowak et al.

(10) Patent No.: US 11,041,920 B2
(45) Date of Patent: Jun. 22, 2021

(54) MR COIL ARRANGEMENT WITH FLEXIBLE COIL SEPARATION LAYER

(71) Applicant: Siemens Healthcare GmbH, Erlangen (DE)

(72) Inventors: Erik Nowak, Cologne (DE); Stephan Zink, Erlangen (DE); Peter Feld, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 250 days.

(21) Appl. No.: 16/013,909

(22) Filed: Jun. 20, 2018

(65) Prior Publication Data

US 2018/0372816 A1 Dec. 27, 2018

(30) Foreign Application Priority Data

Jun. 21, 2017 (DE) .......................... 102017210420.1

(51) Int. Cl.
| | | |
|---|---|---|
| *G01R 33/3415* | (2006.01) | |
| *H01F 27/28* | (2006.01) | |
| *G01R 33/34* | (2006.01) | |
| *A61B 5/055* | (2006.01) | |
| *H01F 27/32* | (2006.01) | |
| *H01F 27/30* | (2006.01) | |

(52) U.S. Cl.
CPC .......... *G01R 33/3415* (2013.01); *A61B 5/055* (2013.01); *G01R 33/34007* (2013.01); *G01R 33/34084* (2013.01); *H01F 27/28* (2013.01); *H01F 27/306* (2013.01); *H01F 27/323* (2013.01)

(58) Field of Classification Search
None
See application file for complete search history.

(56) References Cited

U.S. PATENT DOCUMENTS

2012/0256633 A1   10/2012   Biber et al.
2018/0017643 A1   1/2018    Zink

FOREIGN PATENT DOCUMENTS

| DE | 102011007065 A1 | 10/2012 |
|---|---|---|
| DE | 102016212724 A1 | 1/2018 |
| JP | 2008154933 A | 7/2008 |

OTHER PUBLICATIONS

English Translation of JP 2008154933 to Ishii, 2008 (Year: 2008).*
German Office Action for German Application No. 10 2017 210 420.1 dated Jan. 7, 2019, with English translation.
German Office Action for German Application No. 10 2017 210 420.1 dated Mar. 5, 2018, with English translation.
German Office Action for German Application No. 102017210420.1, dated Mar. 5, 2018.

* cited by examiner

*Primary Examiner* — Douglas X Rodriguez
(74) *Attorney, Agent, or Firm* — Lempia Summerfield Katz LLC

(57) ABSTRACT

A coil arrangement for a magnetic resonance tomography system is provided. The coil arrangement has at least one coil separation layer that includes a matrix that is perforated, single-piece, and planar. The matrix is compression-resistant in a vertical direction relative to a surface of the matrix, but may be adjusted to a curved surface by bending. A method for producing a coil arrangement and a magnetic resonance imaging system are also provided.

19 Claims, 6 Drawing Sheets

MR COIL ARRANGEMENT WITH FLEXIBLE COIL SEPARATION LAYER

This application claims the benefit of German Application No. DE 10 2017 210 420.1, filed on Jun. 21, 2017, which is hereby incorporated by reference in its entirety.

BACKGROUND

The present embodiments relate to a coil arrangement for a magnetic resonance tomography system, a method for producing a coil arrangement, and a magnetic resonance imaging system.

Magnetic resonance tomography systems are imaging apparatuses that, in order to map an examination object, align the nuclear spins of the examination object with a strong external magnetic field and by a magnetic alternating field excite the nuclear spins for precession about this alignment. The precession or return of the spins from this excited state into a state with less energy in turn generates, as a response, a magnetic alternating field (e.g., a magnetic resonance signal) that is received via antennae.

With the aid of magnetic gradient fields, a spatial encoding is impressed onto the signals, which then permits an assignment of the received signal to a volume element. The received signal is then evaluated, and a three-dimensional imaging representation of the examination object is provided.

Magnetic alternating fields with a frequency that corresponds to the Larmor frequency with the respective static magnetic field strength and very high field strengths or outputs are to be provided to excite the precession of the spins. Antennae that are frequently referred to as local coils and are arranged directly on the patient are used to improve the signal-to-noise ratio of the magnetic resonance signal received by the antennae.

The individual patients, however, differ considerably in terms of physiognomy so that with a rigid local coil, an optimal signal is either only received with a few patients or many different local coils in terms of dimensions are to be kept ready.

A general objective with imaging is to bring the coil elements as close as possible to the patient (e.g., the body region to be examined) in order as a result to obtain as good a signal-to-noise ratio as possible. A distinction is conventionally made between rigid coil types adjusted to a respective body region and flexible coil types.

Rigid coils are used, for example, for head examinations and are adjusted optimally to the special anatomy of the head. However, with patients with a small head, a poorer image quality may result since the RX antennae structures are not optimally close to the anatomy.

An inadequate adjustment may be compensated using flexible coil structures; however, there is typically the problem of such arrangements also only being able to reproduce three-dimensional shapings in a restricted manner. This consequently results in bulges and subregions of the coil arrangement sticking out. For example, with cylindrical body shapes such as the knee or elbow, depending on the diameter, a different overlap or a hole is formed between two coil ends. An optimal image quality is thus not achieved.

DE 10 2011 007 065 A1 shows a knee coil, the RX part of which consists of a rigid and flexible combination.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a coil arrangement, with which improved image results may be achieved with different patients or different application regions of the body of the patient, is provided.

The coil arrangement for a magnetic resonance tomography system of one or more of the present embodiments has at least one coil separation layer. A layer between a coil arrangement (e.g., a local coil arrangement) and an examination object or the surroundings of the local coil arrangement may be a coil separation layer, with which a predetermined safety distance is to be maintained between the coils and the examination object or between the coils and the surroundings.

The at least one coil separation layer includes a perforated, single-piece, planar matrix that is compression-resistant in the vertical direction relative to the matrix surface, but may be adjusted to a curved surface by bending. A layer, the thickness of which may not be changed by typical force effect or only by a predetermined comparatively small percentage, may be, in this context, considered as compression-resistant. The perforations allow for increased flexibility of the coil separation layer. As a result of this, the coils of the coil arrangement may be better preformed to a form of an examination object. The compression resistance of the coil separation layer provides the requisite minimum distance of the coil arrangement from the examination object. The distance between the coils and the examination object may therefore be kept constant over a large area. This results in an improved signal-to-noise ratio and consequently in an improved image quality of the magnetic resonance imaging with such a coil arrangement.

With the use of one or more of the present embodiments, a coil arrangement is used to produce a local coil for a magnetic resonance imaging system. The local coil shows the advantages of the coil arrangement of the present embodiments.

With the method for producing a coil arrangement of one or more of the present embodiments, a coil separation layer is generated. The coil separation layer includes a perforated, single-piece, planar matrix that is compression-resistant in the vertical direction relative to the matrix surface, but may be adjusted to a curved surface by bending. The coil arrangement of one or more of the present embodiments that shows the advantages already described is produced with the method of one or more of the present embodiments.

The magnetic resonance imaging system includes the coil arrangement. The magnetic resonance imaging system shares the advantages of the coil arrangement.

The description of one category may also be further developed similarly to the description of another category. Within the context of the present embodiments, the different features of different exemplary embodiments may also be combined to form new exemplary embodiments.

In one possible embodiment of the coil arrangement, the coil separation layer includes a plurality of perforated subregions that are embodied similarly. A regular design of the perforations allows for uniformly distributed flexural properties and deformation properties across the entire surface of the coil separation layer.

In one embodiment of the coil arrangement, the coil arrangement includes a local coil.

The local coil may be adapted to the shape of the examination object, so that the induced magnetic resonance signals may be acquired undamped.

In one possible embodiment of the coil arrangement, the perforated subregions have cutouts that indicate one of the following surface shapes: hexagonal shape, a round shape, a triangular shape, a square shape, a pentagon shape, a heptagon shape, a star shape, or a Y shape.

In one embodiment of the coil arrangement, the cutouts include one of the following types: cuts or planar cutouts.

Small depressions in the separation layer may be cuts that only penetrate one part of the thickness of the layer or pass completely through the entire layer thickness. The flexibility and bendability of the separation layer is increased with the aid of the cuts.

Planar depressions or planar perforations passing through the entire thickness of the separation layer may be cutouts likewise contributing to an improved deformability of the separation layer and allowing for elasticity and extensibility in the direction of the surface plane of the coil separation layer.

In one possible embodiment of the coil arrangement, part of the cutouts of the perforated subregions are embodied such that vertical plug-in connection elements may be fixed into the cutouts in a defined pattern.

In one embodiment of the coil arrangement, the vertical plug-in connection elements are configured to connect the coil separation layer with an external layer and/or a second coil separation layer. The external layer may be fixed to the coil separation layer so that it is possible to prevent the two layers from sliding against one another or the external layer from detaching from the coil separation layer in an undesirable manner. Similarly, a second coil separation layer may also be fixed relative to the first coil separation layer so that a displacement of these two layers against one another is prevented. The local coils of the coil arrangement are then disposed between the two coil separation layers. With the aid of this sandwich arrangement, a defined safety distance may be retained during an imaging procedure both between the coils and the examination object and also between the coils and the support staff.

In one possible embodiment of the coil arrangement, the plug-in connection elements are configured to receive electronic cables, coil cables, and/or electronic components running in the lateral direction. For example, the plug-in connection elements may have passages or continuous cutouts, through which the cited elements may run and simultaneously may be fixed.

In one possible embodiment of the coil arrangement, a plurality of coil cables are embodied in a coil layer. Two coil separation layers are embodied above and below the coil layer, and two external layers are embodied on the two outer faces of the coil separation layers. The plurality of coil cables may be fixed with the aid of the already cited vertical plug-in connection elements, so that the distances between the coils or the coil overlapping regions remain the same even when the coil arrangement is deformed. This achieves a good decoupling between the individual coils or coil loops.

In another embodiment of the coil arrangement, the coil arrangement has at least one (e.g., two) intermediate layer. Each layer of the at least one layer is embodied between a coil separation layer and an external layer and is embodied to allow for a longitudinal displacement of the external layer with respect to the separation layer. Forces that displace the external layer in the longitudinal direction may be shielded from the separation layer so that the separation layer also remains at the desired position from the outside in the event of such an influence or malfunction.

In one embodiment of the method for producing a coil arrangement, the perforated matrix structure is generated by an additive manufacturing method. Additive manufacturing methods include methods in which material is applied at a desired point or in a desired form. A 3D printing method may be applied as an additive method, for example.

Alternatively, the perforated matrix structure may also be generated by a subtractive manufacturing method. With subtractive methods, material is removed from a blank in order to reach the desired structure. With a subtractive method, etching or milling techniques may be used, for example.

DETAILED DESCRIPTION

Figure 1:
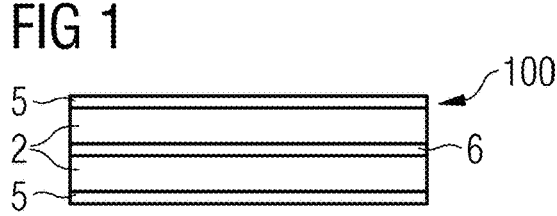
FIG. 1 shows a cross-sectional view of a section of a coil arrangement according to an exemplary embodiment.

FIG. 1 shows a schematic cross-sectional representation of a section 100 of one embodiment of a local coil arrangement that is used to detect magnetic resonance signals. The section 100 is assembled in the manner of a sandwich and has a coil layer 6 in the interior. The coil layer 6 includes a plurality of coil loops (not shown) arranged in a planar manner. The coil layer 6 is surrounded by a separation layer 2 on both sides. Each of the coil separation layers 2 is approximately 5 mm thick and provides a safety distance between an examination object (e.g., a patient) and the coil layer 6. External layers 5 as a protective layer are applied to the two outward facing sides of the separation layers 2.

Figure 2:
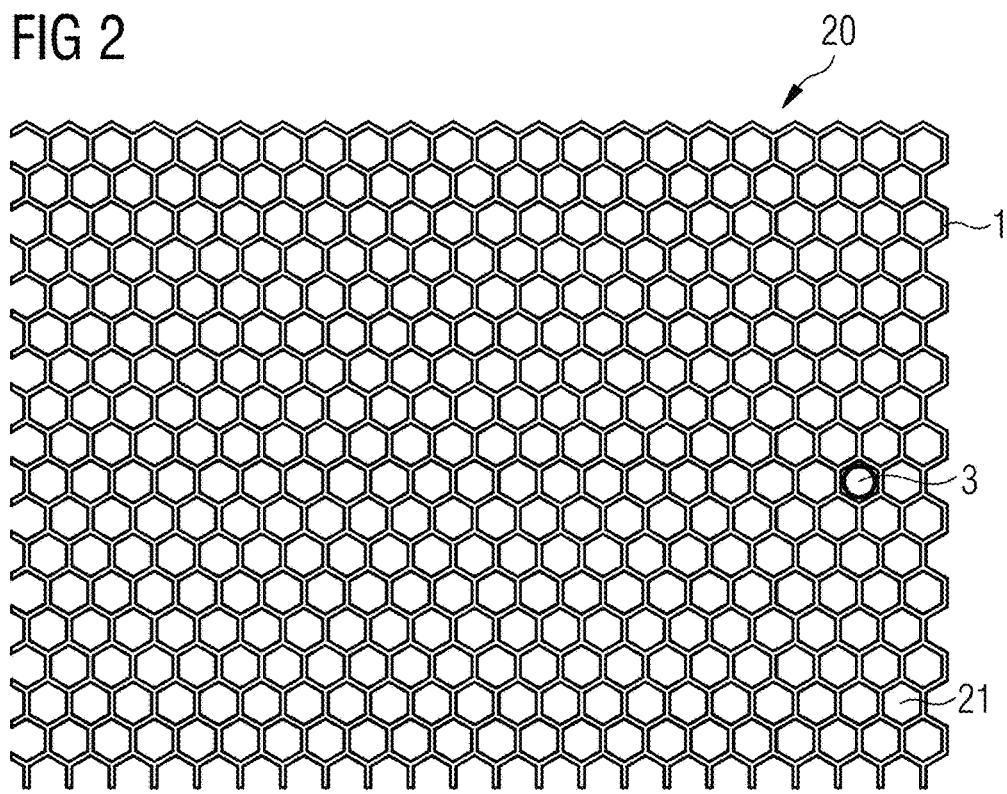
FIG. 2 shows a schematic representation of a separation layer of an embodiment of a coil arrangement.

FIG. 2 shows a schematic representation of a separation layer 20 of an embodiment of a local coil arrangement. The separation layer 20 includes honeycombed cutouts 21 that run continuously through the separation layer 20 in the vertical direction. The separation layer 20 also has circular continuous cutouts 3, into which in the view shown in FIG. 3, vertical plug-in connection elements 9, 10, 11 may be inserted. In a left subregion of FIG. 3, a mushroom-shaped plug-in connection 10 is shown. The mushroom-shaped plug-in connection 10 includes a slotted tubular clamping cylinder 13 that may be inserted into a circular cutout 3 shown in FIG. 2. The mushroom-shaped plug-in connection 10 also includes a disk-shaped head 12, with which further components (e.g., an external layer 5) may be fixed in a force or form-fit manner to the separation layer 20. Alternatively or in addition, a plug-in connection element 11, shown on the right side of FIG. 3, with two slotted tubular clamping cylinders 13 that oppose one another may also be inserted into one of the circular continuous cutouts 3. The plug-in connection element 11 with two slotted tubular clamping cylinders 13 that oppose one another includes a passage 14 that is present between the two clamping cylinders 13, for electrical cables (e.g., coil loops, or electronic components) that may be guided herethrough. The passage 14 may lie in the local coil arrangement according to FIG. 1 in the coil layer 6.

Figure 3:
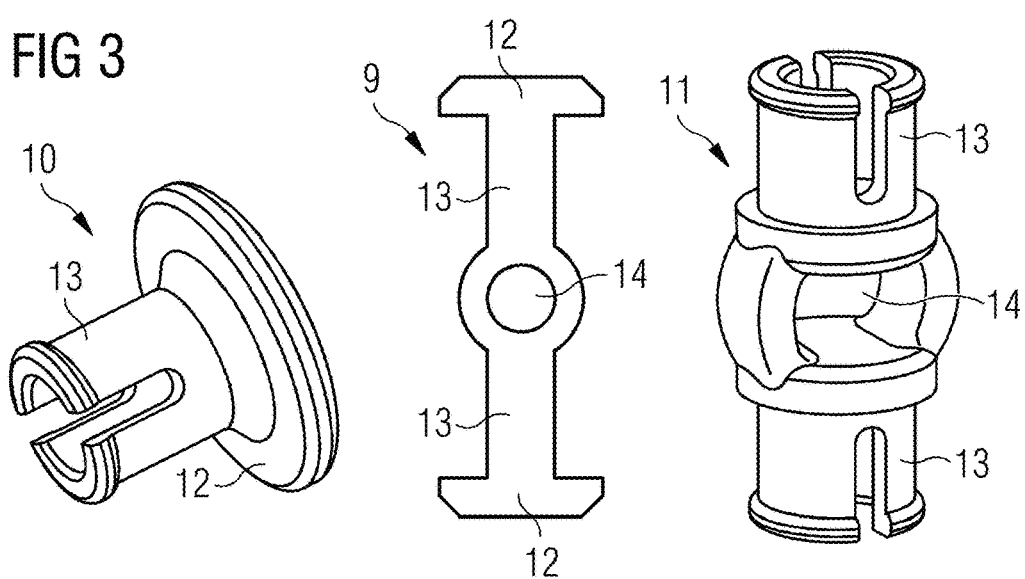
FIG. 3 shows a schematic representation of different plug-in connection elements.

As shown in the central part of FIG. 3, a combined plug-in connection element 9 may also be formed from two mushroom-shaped plug-in connection elements 10 and a plug-in connection element 11 with two slotted tubular clamping cylinders 13 that oppose one another.

Figure 4:
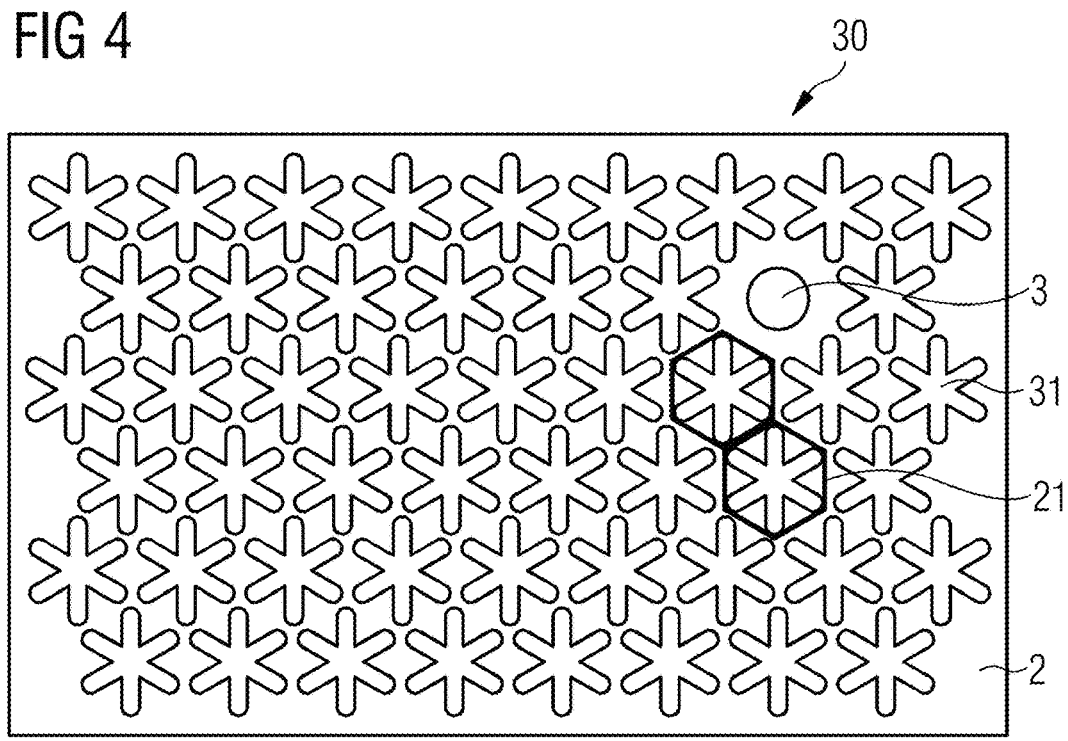
FIG. 4 shows a schematic representation of an alternative embodiment of a separation layer of a coil arrangement.

FIG. 4 shows a separation layer 30 with star-shaped cutouts 31 inscribed into a regular hexagon 21 that are also referred to as "star honeycombs". The star honeycombs 31 are a further development of the embodiment shown in FIG. 2 and only partially reproduce the honeycombed structure in FIG. 2. On account of the remaining triangular/diamond structures, the arrangement in FIG. 4 obtains an end stop that may be adjusted thereby with tensile stress and with pressure or compression loading. An excessive strain on the separation layer 30 may be avoided in this way.

Figure 5:
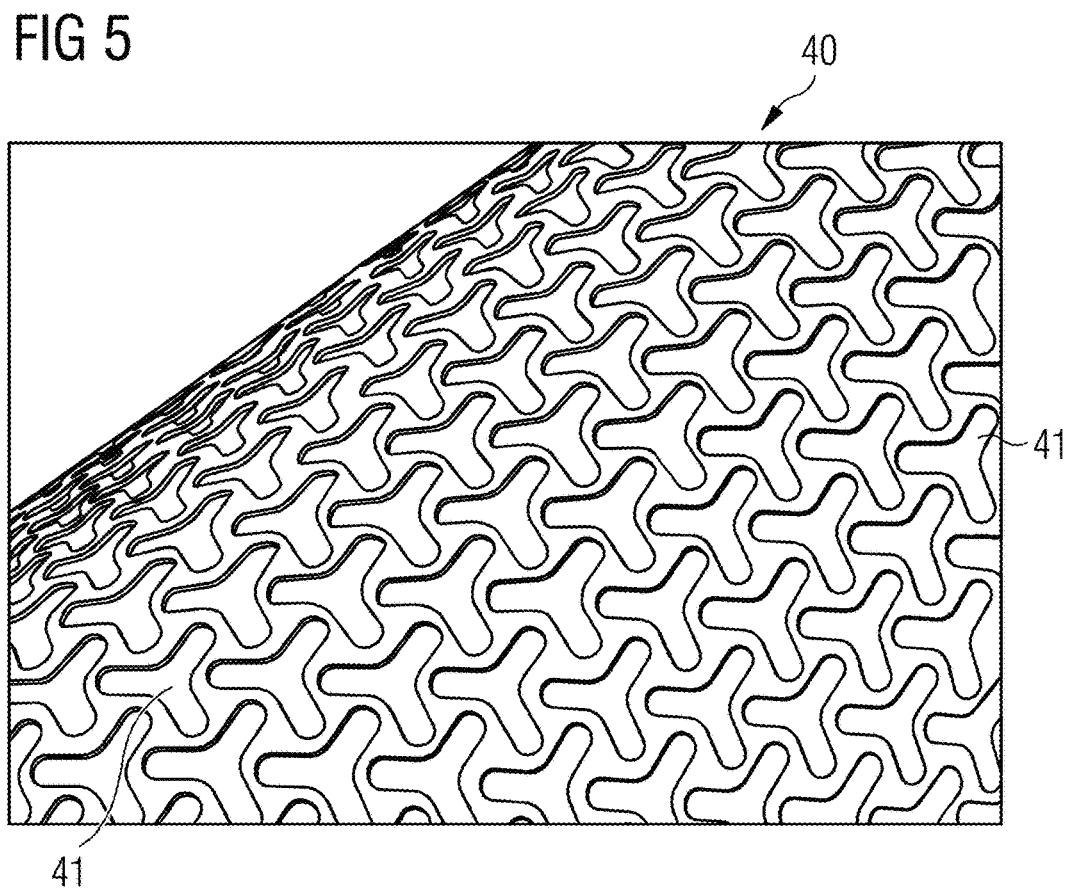
FIG. 5 shows a schematic representation of a further alternative embodiment of a separation layer of a coil arrangement.

FIG. 5 shows a separation layer 40 with cutouts 41 with a Y-structure. With this arrangement, conversely to the predescribed embodiments, an adjustment to a curved structure does not take place via an expansion, but instead via a bending of the remaining structures of the material of the separation layer 40. For safety reasons, the described cutouts 41 or corresponding widths are to be smaller than that through which a finger may pass in the expanded state.

Figure 6:
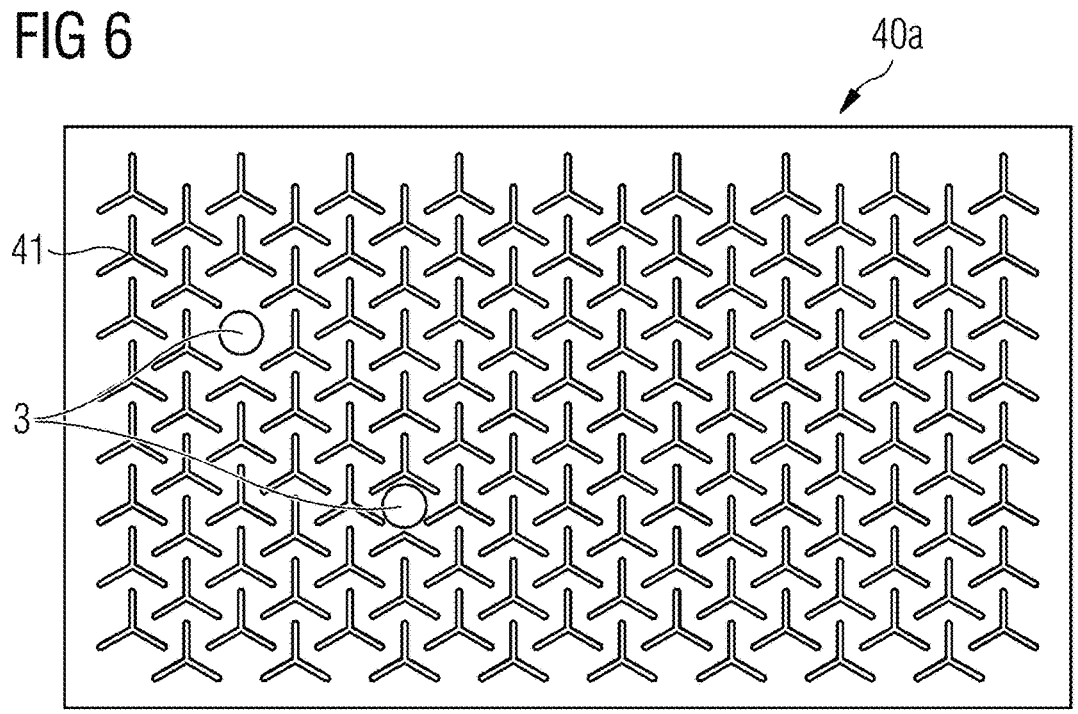
FIG. 6 shows a top view of a separation layer according to an exemplary embodiment.

As apparent in FIG. 6 in a top view of a separation layer 40a, the cutouts 41 may be embodied as cuts instead of as holes. The cuts may expand when the separation layer 40a is lengthening or shaped three-dimensionally, and allow the local coil arrangement to be brought from the planar form into a bulged form with relatively minimal force. As apparent in FIG. 6, individual circular cutouts 3 may be embodied in the separation layer 40a. Plug-in connection elements 9, 10, 11 may be fixed into the individual circular cutouts 3. The plug-in connection elements 9, 10, 11 may connect the separation layer 40a to an external layer, for example.

Figure 7:
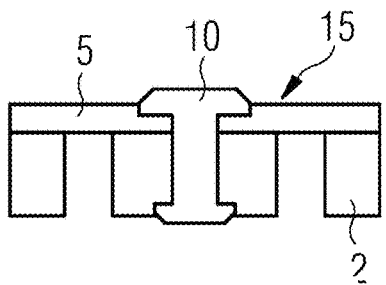
FIG. 7 shows a schematic cross-section through a separation layer of one embodiment of a coil arrangement.

FIG. 7 shows a cross-sectional view of one embodiment of an arrangement 15 from a separation layer 2 and an external layer 5. The separation layer 2 and the external layer 5 are held together with a mushroom-shaped plug-in connection 10.

Figure 8:
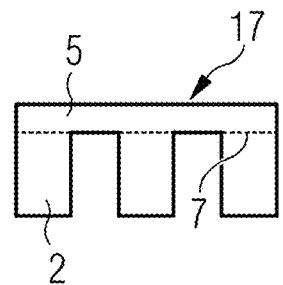
FIG. 8 shows a schematic cross-section through a separation layer of one embodiment of a coil arrangement.

FIG. 8 shows a cross-sectional view of a section 17 of one embodiment of a local coil arrangement from a separation layer 2 and an external layer 5. The separation layer 2 and the external layer 5 are held together by adhesive substances.

Figure 9:
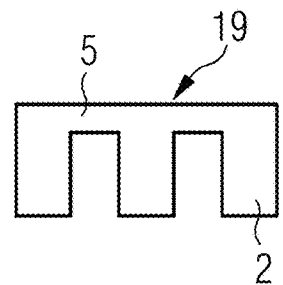
FIG. 9 shows a schematic cross-section through a separation layer of one embodiment of a coil arrangement.

FIG. 9 shows a cross-sectional view of an arrangement 19 including a separation layer 2 and an external layer 5. The separation layer 2 and the external layer 5 are embodied in one piece and may be produced with the aid of a stamping process, a contour-cutting process, or a casting process, for example. In this case, the external layer 5 has the same material property as the separation layer 2.

Figure 10:
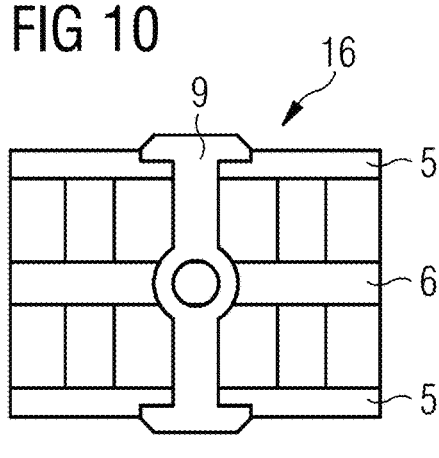
FIG. 10 shows a schematic cross-section through a separation layer of one embodiment of a coil arrangement.

FIG. 10 shows a cross-sectional view of one embodiment of a local coil arrangement 16. The local coil arrangement 16 includes an internal coil layer 6 that includes local coils and electronic components. Coil separation layers 2, also known as separation layers 2, are each embodied below and above the coil layer 6 and provide a separation from the coil layer 6. The separation layers 2 are each shielded outwardly from an external layer 5. The layer arrangement 16 is held together by combined plug-in connections 9, as illustrated already in FIG. 3.

Figure 11:
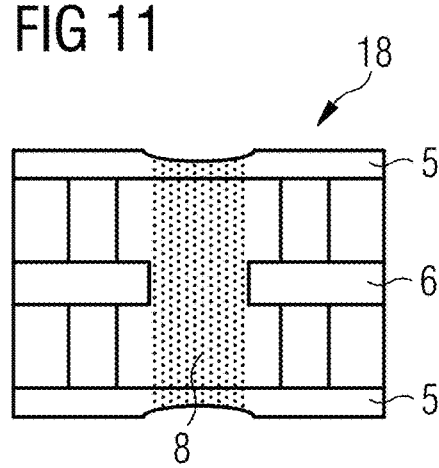
FIG. 11 shows a schematic cross-section through a separation layer of one embodiment of a coil arrangement.

FIG. 11 shows a cross-sectional view of one embodiment of a local coil arrangement 18. The local coil arrangement 18 includes an internal coil layer 6. The internal coil layer 6 includes local coils and electronic components. Separation layers 2 that provide a distance from the coil layer 6 are each embodied below and above the coil layer 6. The separation layers 2 are each shielded outwardly from an external layer 5. The layer arrangement 16 is held together by a thermal welding 8 of the external layer 5 and separation layer 2. The welding 8 also fixes the electronics of the coil layer 6.

Figure 12:
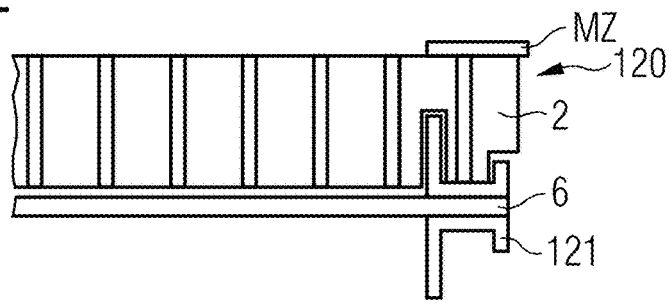
FIG. 12 shows a cross-sectional view of one embodiment of a coil arrangement assembled layer by layer.

FIG. 12 shows a cross-sectional view of one embodiment of a local coil arrangement 120. The local coil arrangement 120 includes a local coil layer 6, a separation layer 2, and an external layer 5. The local coil layer 6, also known as antenna layer, is protected toward the edge with a frame 121. A material additive MZ, with which a sealing function is achieved, is applied to the external layer 5 at the edge (e.g., on the right side in the image).

Figure 13:
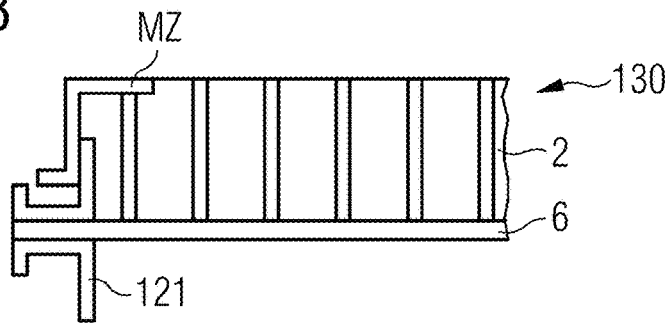
FIG. 13 shows a cross-sectional view of an alternative embodiment of a coil arrangement assembled layer by layer.

FIG. 13 shows a cross-sectional view of one embodiment of a local coil arrangement 130. The local coil arrangement 130 includes a local coil layer 6, a separation layer 2, and an external layer 5. The antenna layer 6 is protected toward the edge with a frame 121. A material additive MZ, which runs in the vertical direction up to the frame 121 and with which a sealing function is achieved, is applied to the external layer 5 at the edge (e.g., on the left side in the image).

Figure 14:
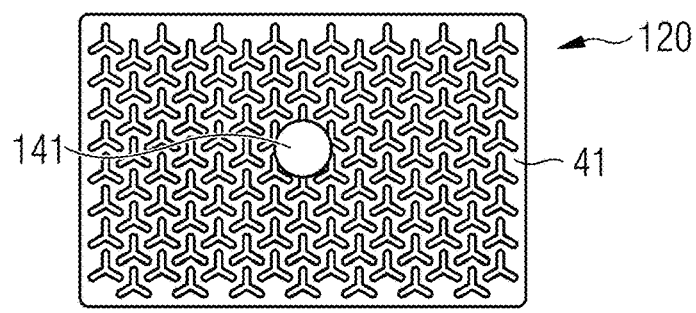
FIG. 14 shows a top view of one embodiment of a coil arrangement assembled layer by layer and produced as bulk stock.

A top view of a local coil arrangement 120 embodied as bulk stock is shown in FIG. 14. Cutouts 41 embodied in a Y shape are distributed across the entire surface of the arrangement 120. A circular cutout 141, which may be used as an opening for feeding through a body part, for example, is located in the center of the arrangement 120. The frame, already shown in FIG. 12 and FIG. 13, combined with the material additive may serve as a boundary for this cutout 141, for example. These elements also then serve to achieve a sealing of the series of layers of the local coil arrangement, if, as shown in FIG. 14, individual y-shaped cutouts 41 are cut or damaged by the stamping of the circular cutout 141. The bulk stock may be cut accordingly for a specific application. Upon final assembly, the edges are then sealed for sealing with the aid of the frame 121 described and the material additive MZ already illustrated.

Figure 15:
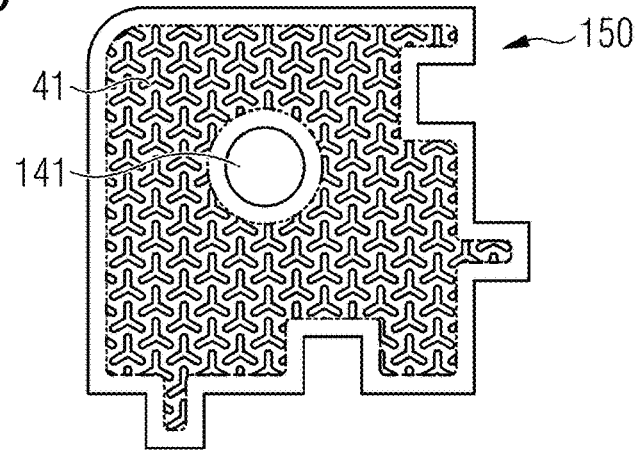
FIG. 15 shows a top view of one embodiment of a coil arrangement assembled layer by layer and produced as a puzzle.

FIG. 15 shows a top view of one embodiment of a local coil arrangement 150 as a puzzle piece. Cutouts 41 embodied in a Y shape are distributed across the entire surface of the arrangement 150. A circular cutout 141, which may be used as an opening for feeding through a body part, for example, is located in the center of the arrangement 150. In this variant, a sealing boundary does not subsequently need to be generated, since with a special application, the puzzle pieces are not changed. Instead, only suitable puzzle pieces are stuck together to form a larger arrangement.

Figure 16:
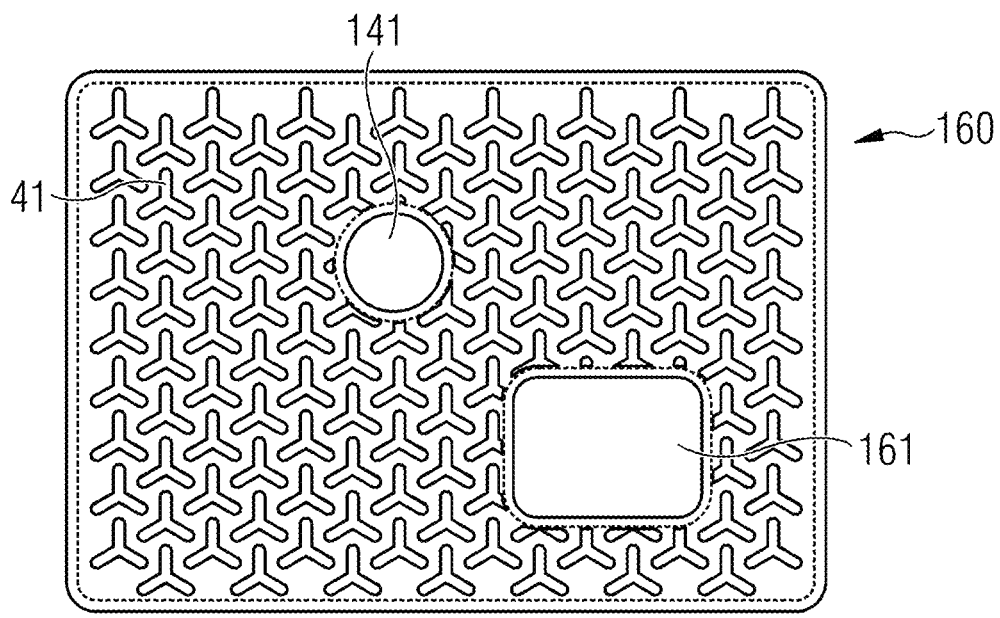
FIG. 16 shows a top view of one embodiment of a coil arrangement assembled layer by layer and adjusted to a special application.

FIG. 16 shows a top view of one embodiment of a local coil arrangement 160 that is embodied as an individual product-specific embodiment. Cutouts 41 embodied in a Y shape are distributed across the entire surface of the arrangement 160. A circular cutout 141, which may be used as an opening for feeding through a body part, for example, is located in the center of the arrangement 160. A rectangular cutout 161 is also shown on the right side of the local coil arrangement 160. The cutouts 141, 161 are determined in a product-specific manner. In this embodiment, there is no subsequent provision to adjust the cutouts 141, 161 to a specific geometry. No additional frame 121 or material additives MZ are then also to be applied.

Figure 17:
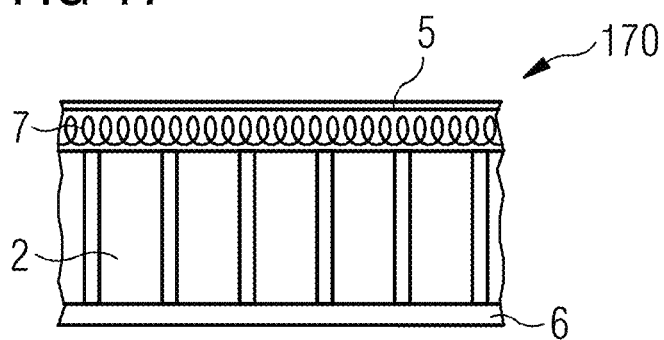
FIG. 17 shows a cross-sectional view of one embodiment of a coil arrangement assembled layer by layer with an intermediate layer.

FIG. 17 shows a cross-sectional view of one embodiment of a local coil arrangement 170 with an intermediate layer 7. An intermediate layer 7 that serves to allow for a longitudinal displacement of the separation layer 2 and external layer 5 against one another is located between the separation layer 2 and the external layer 5.

For the sake of simplicity in FIG. 17, a separation layer 2 is only shown on one side of the coil layer 6. A separation layer, a further intermediate layer, and an external layer are generally also disposed on the other side of the coil layer 6 in order to protect the coil 6 toward both sides.

Figure 18:
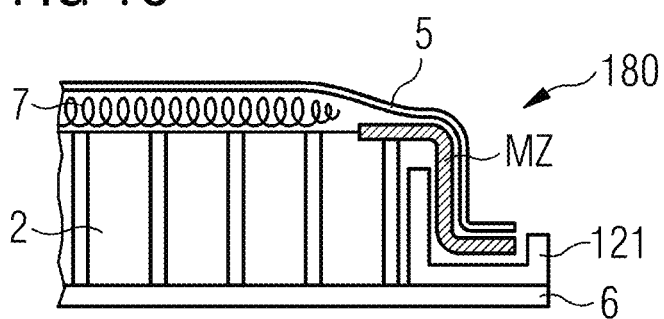
FIG. 18 shows a cross-sectional view of one embodiment of a coil arrangement assembled layer by layer with a frame and a material additive.

FIG. 18 shows a cross-sectional view of one embodiment of a local coil arrangement 180 that, similarly to the local coil arrangement 170 shown in FIG. 17, has an intermediate layer 7 between the external layer 5 and the separation layer 2. In this variant, a coil layer 6 shielded from the separation layer 2 is provided at the edge with a frame 121. The separation layer 2 is sealed toward the edge with the aid of a material additive MZ.

Figure 19:
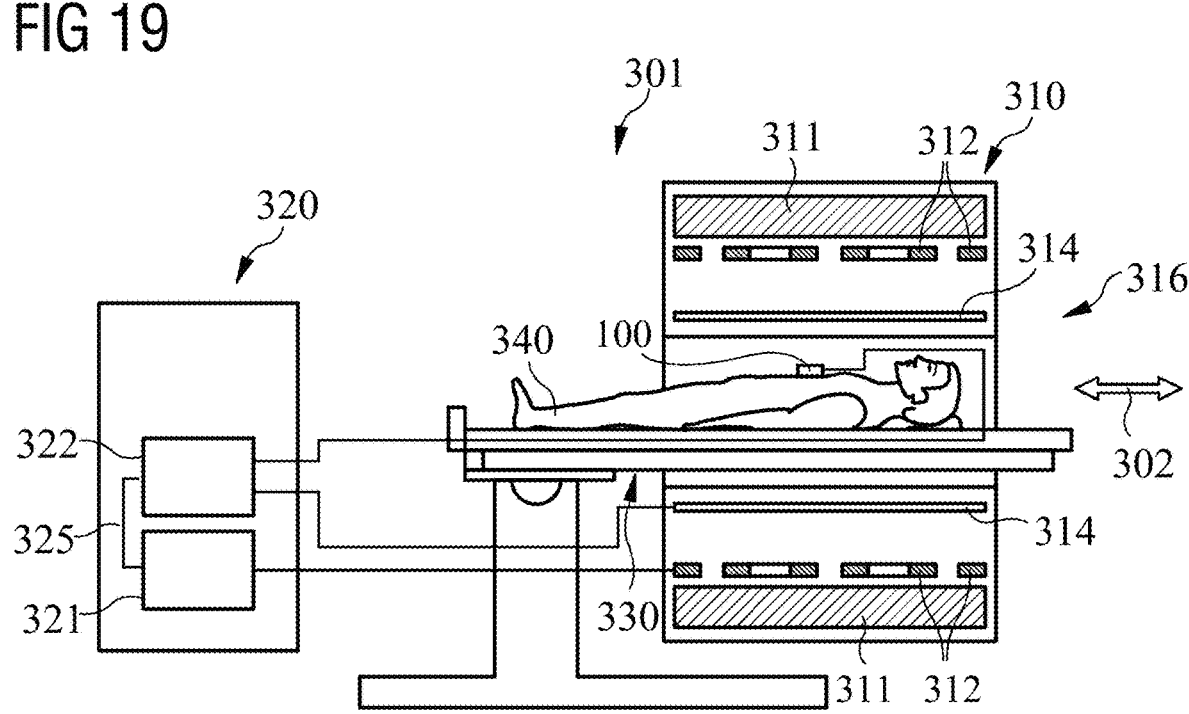
FIG. 19 shows a schematic representation of one embodiment of a magnetic resonance imaging system.

FIG. 19 shows a schematic representation of an embodiment of a magnetic resonance tomography system 301 with a local coil arrangement 100 of one or more of the present embodiments.

The magnet unit 310 has a field magnet 311 that generates a static magnetic field B0 for aligning the nuclear spins of specimens or in a body of a patient 340 in a recording region. The recording region is arranged in a patient tunnel 316 that extends in a longitudinal direction 302 through the magnet unit 310. Typically, the field magnet 311 involves a superconducting magnet that may provide magnetic fields with a magnetic flux density of up to 3T or even higher in the latest devices. For lower field strengths, however, permanent magnets or electromagnets with normal-conducting coils may also be used.

The magnet unit 310 has gradient coils 312 that are configured to overlay the magnetic field B0 with variable magnetic fields in three spatial directions for the spatial differentiation of the acquired imaging regions in the examination volume. The gradient coils 312 are normally coils made of normal-conducting wires that may generate fields orthogonal to one another in the examination volume.

The magnet unit 310 likewise has a body coil 314 that is configured to release a radio-frequency signal fed via a signal line into the examination volume and to receive resonance signals emitted by the patient 340 and output the resonance signals via the signal line. The magnetic resonance tomography system of one or more of the present embodiments has one or more local coil arrangements 100 according to an exemplary embodiment. The one or more local coil arrangements 100 are arranged in the patient tunnel 316 close to the patient 340.

A control unit 320 supplies the magnet unit 310 with the various signals for the gradient coils 312 and the body coil 314 and evaluates the signals received.

Thus, the control unit 320 has a gradient control 321 configured to provide the gradient coils 312 with variable currents via supply lines. The variable currents provide the desired gradient fields in the examination volume on a temporally coordinated basis.

The control unit 320 has a radio-frequency unit 322 configured to generate a radio-frequency pulse with a predetermined time characteristic, amplitude, and spectral power distribution to excite a magnetic resonance of the nuclear spins in the patient 340. In this case, pulse powers in the kilowatt range may be achieved. The individual units are connected with one another via a signal bus 325.

The radio-frequency signal generated by the radio-frequency unit 322 is fed to the patient couch 330 via a signal connection, and distributed to one or more local coils and transmitted into the body of the patient 340, in order there to excite the nuclear spins.

The local coil of the local coil arrangement 100 may then receive a magnetic resonance signal from the body of the patient 340, since, due to the minimal distance, the signal-to-noise ratio (SNR) of the local coil is better than upon receipt by the body coil 314. The MR signal received by the local coil is prepared in the local coil and forwarded to the radio-frequency unit 322 of the magnetic resonance tomography system 301 for evaluation and image detection purposes. Similarly, the signal connection may be used, but separate signal connections or a wireless transmission may also be provided, however. In one embodiment, separate local coils or other antennae are provided for the reception.

The devices and methods described above are merely exemplary embodiments of the invention, and the invention may also be varied by a person skilled in the art without departing from the scope of the invention as defined by the claims. The use of the indefinite article "a" or "an" does not preclude the relevant features from also being present plurally. Similarly, the expression "unit" does not preclude this consisting of a plurality of components that may also be spatially distributed.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A coil arrangement for a magnetic resonance tomography system, the coil arrangement comprising:
a coil separation layer configured to be coupled to a coil layer, the coil separation layer comprising a planar matrix, the planar matrix being a single piece and perforated in a regular design distributed across a substantial portion of a surface of the planar matrix, the planar matrix being compression-resistant in a vertical direction relative to the surface of the planar matrix, but being adjustable to a curved surface by bending.

2. The coil arrangement of claim 1, wherein the coil separation layer comprises a plurality of perforated subregions that are configured to be the same.

3. The coil arrangement of claim 2, wherein the plurality of perforated subregions have cutouts that have a surface shape that is a hexagon, round, triangular, a square, a pentagon, a heptagon, a star, or a Y shape.

4. The coil arrangement of claim 3, wherein the cutouts include cuts or continuous cutouts.

5. The coil arrangement of claim 3, wherein one part of the cutouts of the plurality of perforated subregions is configured such that vertical plug-in connection elements are fixable into the cutouts in a defined pattern.

6. The coil arrangement of claim 5, wherein the vertical plug-in connection elements are configured to connect the coil separation layer with an external layer, a second coil separation layer, or the external layer and the second coil separation layer.

7. The coil arrangement of claim 5, wherein the plug-in connection elements are configured to receive electronic cables, electronic components running in a lateral direction, or the electronic cables and the electronic components running in the lateral direction.

8. The coil arrangement of claim 7, further comprising:
two intermediate layers configured between the coil separation layer and an external layer, the two intermediate layers being configured to allow for a longitudinal displacement of the external layer relative to the coil separation layer.

9. The coil arrangement of claim 1, further comprising a local coil.

10. The coil arrangement of claim 1, wherein the coil separation layer is a first coil separation layer,
wherein the coil arrangement further comprises:
a plurality of coil lines configured in the coil layer;
a second coil separation layer, the first coil separation layer and the second coil separation layer being configured above and below the coil layer; and
two external layers configured on two outer faces of the first coil separation layer and the second coil separation layer, respectively.

11. A method for producing a coil arrangement, the method comprising:
generating a coil separation layer configured to be coupled to a coil layer, the coil separation layer comprising a planar matrix, the planar matrix being a single piece and perforated in a regular design distributed across a substantial portion of a surface of the planar matrix, the planar matrix being compression-resistant in a vertical direction relative to the surface of the planar matrix, but being adjustable to a curved surface by bending.

12. The method of claim 11, wherein generating the coil separation layer comprises generating a structure of the planar matrix by an additive manufacturing method.

13. The method of claim 11, wherein generating the coil separation layer comprises generating a structure of the planar matrix by a subtractive manufacturing method.

14. A magnetic resonance imaging system comprising:
a coil arrangement comprising:
a coil separation layer configured to be coupled to a coil layer, the coil separation layer comprising a planar matrix, the planar matrix being a single piece and perforated in a regular design distributed across a substantial portion of a surface of the planar matrix, the planar matrix being compression-resistant in a vertical direction relative to the surface of the planar matrix, but being adjustable to a curved surface by bending.

15. The magnetic resonance imaging system of claim 14, wherein the coil separation layer comprises a plurality of perforated subregions that are configured to be the same.

16. The magnetic resonance imaging system of claim 15, wherein the plurality of perforated subregions have cutouts that have a surface shape that is a hexagon, round, triangular, a square, a pentagon, a heptagon, a star, or a Y shape.

17. The magnetic resonance imaging system of claim 16, wherein one part of the cutouts of the plurality of perforated subregions is configured such that vertical plug-in connection elements are fixable into the cutouts in a defined pattern.

18. The magnetic resonance imaging system of claim 17, wherein the vertical plug-in connection elements are configured to connect the coil separation layer with an external layer, a second coil separation layer, or the external layer and the second coil separation layer.

19. The magnetic resonance imaging system of claim 14, wherein the coil arrangement further comprises a local coil.

* * * * *